US009776171B2

(12) United States Patent
Hanau et al.

(10) Patent No.: US 9,776,171 B2
(45) Date of Patent: Oct. 3, 2017

(54) HOUSEHOLD APPLIANCE HAVING A CATALYTICALLY EFFECTIVE SURFACE AND METHOD FOR THE OPERATION THEREOF

(71) Applicant: BSH HAUSGERÄTE GMBH, München (DE)

(72) Inventors: Andreas Hanau, Berlin (DE); Antonio Barrado Franco, Berlin (DE); Andreas Bischof, Berlin (DE); Hartmut Schaub, Brieselang (DE)

(73) Assignee: BSH Hausgeräte GmbH, Munich (DE)

( * ) Notice: Subject to any disclaimer, the term of this patent is extended or adjusted under 35 U.S.C. 154(b) by 115 days.

(21) Appl. No.: 14/780,127

(22) PCT Filed: Feb. 26, 2014

(86) PCT No.: PCT/EP2014/053751
§ 371 (c)(1),
(2) Date: Sep. 25, 2015

(87) PCT Pub. No.: WO2014/154432
PCT Pub. Date: Oct. 2, 2014

(65) Prior Publication Data
US 2016/0045897 A1    Feb. 18, 2016

(30) Foreign Application Priority Data
Mar. 26, 2013   (DE) .................. 10 2013 205 302

(51) Int. Cl.
| | | |
|---|---|---|
| *B01J 23/30* | (2006.01) | |
| *B01J 23/22* | (2006.01) | |
| *B01J 21/06* | (2006.01) | |
| *D06F 35/00* | (2006.01) | |
| *A47J 31/44* | (2006.01) | |
| *F24C 15/20* | (2006.01) | |
| *H05B 6/64* | (2006.01) | |
| *A61L 2/232* | (2006.01) | |
| *A47L 15/42* | (2006.01) | |
| *F24C 15/00* | (2006.01) | |
| *D06F 58/20* | (2006.01) | |
| *A47J 17/02* | (2006.01) | |
| *A47J 19/02* | (2006.01) | |
| *F25D 23/00* | (2006.01) | |
| *A01N 59/16* | (2006.01) | |
| *A61L 2/238* | (2006.01) | |
| *A61L 9/18* | (2006.01) | |

(52) U.S. Cl.
CPC ............. *B01J 23/22* (2013.01); *A01N 59/16* (2013.01); *A47J 17/02* (2013.01); *A47J 19/02* (2013.01); *A47J 31/4403* (2013.01); *A47L 15/42* (2013.01); *A61L 2/232* (2013.01); *A61L 2/238* (2013.01); *B01J 21/06* (2013.01); *B01J 21/063* (2013.01); *B01J 23/30* (2013.01); *D06F 35/008* (2013.01); *D06F 58/20* (2013.01); *F24C 15/00* (2013.01); *F24C 15/005* (2013.01); *F24C 15/20* (2013.01); *F25D 23/00* (2013.01); *H05B 6/64* (2013.01); *H05B 6/6402* (2013.01); *A47L 15/4251* (2013.01); *A61L 9/18* (2013.01); *A61L 2202/11* (2013.01); *A61L 2202/23* (2013.01); *A61L 2209/21* (2013.01); *C02F 2303/20* (2013.01); *C02F 2307/12* (2013.01)

(58) Field of Classification Search
CPC ...... A47L 15/4236; A47L 15/42; A61L 2/232; A61L 2/238; A61L 9/18; A61L 2202/11; A61L 2202/23; A61L 2209/21; B01J 21/06; B01J 21/063; B01J 23/22; B01J 23/30; D06F 35/00; D06F 35/0038; D06F 58/20; F24C 15/00; F24C 15/005; F24C 15/20; F25D 23/00; H05B 6/64; H05B 6/6402; C02F 2303/20; C02F 2307/12
See application file for complete search history.

(56) References Cited

U.S. PATENT DOCUMENTS

| | | | |
|---|---|---|---|
| 2007/0051667 A1* | 3/2007 | Martinie ................. | C10G 27/00 208/208 R |
| 2007/0254824 A1* | 11/2007 | Coke .................... | C11D 3/0052 510/406 |
| 2012/0055513 A1* | 3/2012 | Eglmeier ................ | A47L 15/42 134/22.1 |

FOREIGN PATENT DOCUMENTS

| | | |
|---|---|---|
| CN | 1636498 A | 7/2005 |
| CN | 101525746 A | 9/2009 |
| CN | 102449226 A | 5/2012 |
| DE | 10 2009 026712 | 12/2010 |
| EP | 0 761 809 | 3/1997 |
| KR | 2007-0066334 | 6/2007 |

OTHER PUBLICATIONS

Weiping Wang, Chinese Outstanding Master Dissertations Full-Text Databases, "Research on Catalyst Performance of Load-Type Polyoxometalate," Dec. 2011, Published Dec. 15, 2011, B014-128 (pp. 7-9).
International Search Report for PCT/EP2014/053751 dated Jul. 10, 2014.

* cited by examiner

*Primary Examiner* — Saeed T Chaudhry
(74) *Attorney, Agent, or Firm* — Nixon & Vanderhye P.C.

(57) ABSTRACT

The invention relates to a household appliance, which comprises at least one catalytically effective substance in a surface, wherein the catalytically effective substance is a polyoxometalate that is comprised in an inner an/or outer surface of the household appliance, provided that the polyoxometalate is comprised at least in an outer surface of the household appliance if the household appliance is a water-bearing household appliance having a container for receiving objects to be cleaned. The invention further relates to a method for operating the household appliance.

15 Claims, No Drawings

HOUSEHOLD APPLIANCE HAVING A CATALYTICALLY EFFECTIVE SURFACE AND METHOD FOR THE OPERATION THEREOF

This application is the U.S. national phase of International Application No. PCT/EP2014/053751 filed 26 Feb. 2014 which designated the U.S. and claims priority to DE Patent Application No. 10 2013 205 302.9 filed 26 Mar. 2013, the entire contents of each of which are hereby incorporated by reference.

The invention relates to a household appliance, which contains at least one catalytically effective substance in a surface, and to a preferred method for the operation thereof.

Household appliances can come into contact with dust, dirt, food, moisture or living beings such as humans or animals. This can result in hygiene problems, since microorganisms can accumulate and propagate on the household appliances. In particular, it can result in contaminated, no longer hygienically faultless household appliances, or at least in household appliances which have unsightly discolorations. In the worst case, this may be a health hazard. Regular cleaning of household appliances is therefore useful, wherein the simplicity and efficiency of such cleaning can depend on the type and quantity of contamination with microorganisms. In some instances a biofilm may form or already be present. Biofilms which consist of organic substances such as microorganisms and nutrients result in nuisance odors and/or visible contamination.

This is particularly relevant in household appliances in which inner and/or outer surfaces come into contact with food, which is stored, processed or prepared in the household appliance for instance.

Other household appliances, which may tend towards contamination with microorganisms, are however also extractor hoods and vacuum cleaners for instance.

In water-bearing household appliances, objects which are contaminated in different ways are generally cleaned. Thus food residues fall into dishwashers and the spectrum of contamination in the case of laundry items to be cleaned in washing machines generally becomes larger and larger. Common to all water-bearing household appliances is that contamination can develop and accumulate in moist warm atmospheres, particularly on less accessible points. This contamination can form a good nutrient base for microorganisms such as bacteria or fungus.

Irrespective of the type of household appliance, there is generally the problem that for operation purposes a control unit of the household appliance must generally be touched by a user. As a result, control units can in particular be contaminated with microorganism, which can be easily passed on during use of the household appliance by different users.

A further problem consists in microorganisms propagating more easily and quickly in a damp atmosphere. This is particularly the case in poorly ventilated areas, which are moreover frequently hard to access. For instance, in the case of a refrigerator, the occurrence of condensed water may promote the growth of microorganisms. Nevertheless, stores for liquids such as water and milk, for instance in coffee machines, are areas which are principally prone to the growth of microorganisms.

It would therefore be desirable to provide a household appliance which can be easily and efficiently cleaned and/or with which the formation of biofilms is prevented as much as possible.

In order to eliminate and/or prevent biofilms, different measures are known. In particular, appliance cleaning programs are offered, which eliminate impurities in water-bearing household appliances at high temperatures with the assistance of detergents and in part with a raised washing liquor level and/or with an increased drum speed, i.e. with the increased input of mechanical energy. The use of ozone to remove organic contamination is also known.

It was similarly already proposed to eliminate organic contamination with the aid of UV-C radiation in the continuous flow principle, wherein the elimination takes place in such a way that microorganisms in such contamination are ultimately killed by damaging their genetic makeup. Photocatalytic methods are likewise known, for instance the use of titanium oxide coatings for deodorizing, disinfecting and cleaning purposes. Activation of the catalyzer by means of UV radiation is required here.

Measures for killing microorganisms using $Ag+$ or $Cu+$ ions in the washing liquor or on the surfaces of materials in contact with the washing liquor are likewise known.

Other methods focus on the thermal eradication of potentially existing microorganisms by increasing the temperature on the surfaces of the components by way of a direct or indirect energy transmission (water, steam, microwaves).

These known methods and measures are disadvantageous in terms of the high energy outlay and the high apparatus and/or operating costs required in some instances to achieve sufficiently large effects. The use of $Ag+$ or $Cu+$ ions also involves disadvantageous effects with respect to soil and water pollution. With some methods, aggressive means are used, e.g. ozone or UV radiation, so that additional safety measures may be required.

Polyoxometalates are used in different fields, for instance in analytical and clinical chemistry, in catalysis (including photocatalysis), in biochemistry (inhibiting electron transfer processes), in medicine (antitumor and antiviral activity) and in the manufacture of integrated circuits. Polyoxometalates are above all known in the paper and plastics industry as oxidizing catalyzers.

The use of polyoxometalates as bleach catalysts in the household is known. With bleach, the structure of a colorant dye is destroyed by means of a strong oxidizing agent (bleach). Bleaches based on oxygen are above all known, such as peroxide and bleach based on chlorine. In order to enhance the effect of the relatively mild oxygen-based bleaches, particularly at washing temperatures up to 60° C., the use of bleach activators and/or bleach catalyzers is known.

EP 0 761 809 B1 describes a bleach composition which contains polyoxometalates as bleach catalyzers. In such cases small quantities of polyoxometalates already increase the efficiency of bleaches such as hydrogen peroxide, inorganic and organic peracids or caroats. The described bleach composition includes bleach (peroxide) and bleach catalyzers (polyoxometalate) and can be used for instance in detergents, cleaning agents, disinfectant agents and cleaning solutions.

EP 1 141 210 B1 describes a method of bleaching laundry or household surfaces, in which a detergent containing polyoxometalate is brought into contact with the contaminated substrate. In such cases, air is used as the primary source of oxygen atoms for bleaching.

WO 2005/059226 A1 describes a method for washing laundry in a washing machine, wherein the ion strength of the water is changed during a washing cycle in order to optimize the cleaning ability of the water. In such cases the detergent water can contain a bleaching agent system. Inorganic polyoxometalates are described in this context as bleaching oxidizing catalyzers with peroxide bleaching agents and air.

DE 10 2009 026 712 describes a household appliance having at least one component which has a surface which can be loaded by an organic impurity, wherein the surface comprises a photocatalyzer. A photo source for irradiating the photocatalyzer with an activating electromagnetic radiation is assigned to this surface, wherein the surface is formed by a primary shaped first tool, in which the photocatalyzer is disperged. Materials with titanium dioxide and its modifications are described in detail as photocatalyzers.

Against this background the object of the present invention was to provide a household appliance and a method for its operation, in which contamination can be eliminated or prevented easily and particularly hygienically or can be at least largely eliminated or prevented. Contamination with microorganisms is preferably to be eliminated or prevented.

This object is achieved in accordance with the invention by a household appliance and by a method for the operation thereof having the features of the corresponding independent claims. Preferred embodiments of the inventive household appliance are cited in the corresponding dependent claims. Preferred embodiments of the inventive household appliance correspond to preferred embodiments of the inventive method and vice versa, even if this is not explicitly determined herein.

The subject of the invention is thus a household appliance, which contains at least one catalytically effective substance in a surface, wherein the catalytically effective substance is a polyoxometalate, which is contained in an inner and/or outer surface of the household appliance, provided that the polyoxometalate is contained at least in an outer surface of the household appliance, if the household appliance is a water-bearing household appliance with a container for receiving objects to be cleaned.

An "outer surface" of the household appliance here is generally a surface which is accessible for a user of the household appliance during conventional operation of the household appliance, without interfering with the operation. This generally means that an outer surface of the household appliance can be touched and observed without interfering with the operation of the household appliance. Conversely hereto, an "inner surface" of the household appliance is generally a surface which is not accessible to a user of the household appliance during conventional operation of the household appliance, without interfering with the operation. "Inner surfaces" within the meaning of the invention are therefore for instance also the inner surface of a water container of a coffee machine or the inside of a refrigerator. "Outer surfaces" are therefore in particular control elements and the housing of the household appliance.

Polyoxometalates are inorganic metal oxygen clusters. They generally exhibit polyatomic anions, which are made of three or more transition metal oxyanions, in particular wolframate, molybdate, vanadate, niobate and/or tantalate and are bridged via oxygen atoms. Polyoxometalates can form a large three-dimensional network structure with defined oligomer or polymer structural units.

In accordance with their structure, the polyoxometalates are divided into iso- and heteropolyoxometalates. Isopolyoxometalates are the simplest forms of polyoxometalates and can be described as binary, i.e. oxide anions containing only metal ions and oxygen. Typical examples of such isopolyoxometalates are $[Mo_2O_7]^{2-}$, $[W_6O_{24}]^{12-}$, $[Mo_6O_{16}]^{2-}$, $[Mo_{36}O_{112}]^{8-}$. Contrary to this, heteropolyoxometalates, which are used to a large degree as oxidizing catalyzers, contain even more non-metal, half-metal and/or transition metal ions. Therefore, transition metal doped, so-called Keggin anions of the formula $[APW_{11}O_{39}]^{7-/8--}$ with A=Zn, Co, Ni, Mn and Dawson anions $[AP_2W_{17}O_{61}]^{7-/8}$ with A=Mn, Fe, Co, Ni, Cu are known, which may also have bound chemically combined water. Further substitutions, also different transition metal ions, are known, e.g. $[WZnMn_2(ZnW_9O_{34})_2]^{12-}$ or $[SiV_3W_9O_{40}]^{7-}$. The charge balancing of the afore-described anions either takes place by way of protons, wherein the corresponding polyacids are contained, or by way of cations by forming the salts of the polyacids (heteropolyoxometalate).

The term polyoxometalate used herein includes both the salts of the polyacids and also the corresponding polyacids. The afore-cited polyoxometalate and for instance the polyoxometalates described in EP 0761 809 B1 and EP 1 141 210 B1 form part of the inventively used polyoxometalates.

The polyoxometalate is preferably a wolframate. This can be an isopolywolframate or a heteropolywolframate. A titanium-modified wolframate or vanadium-modified wolframate is used particularly preferably. In accordance with the invention it is particularly preferred for the wolframate to contain vanadium. The wolframate here preferably includes the $[SiV_3W_9O_{40}]^{7-}$ anion.

In accordance with the invention the polyoxometalates are preferably present as salts, which consis of a suitable cation and a polyoxometalate anion or include the same. Suitable cations are for instance tetra-alkylammonium cations. By suitably selecting the anion and cation, polyoxometalates can be made available, which can be used as a coating of an inner and/or outer surface of the household appliance. The polyoxometalate is preferably at least partially present as a tetra-alkylammonium salt.

In a preferred embodiment of the household appliance, the outer surface containing at least one polyoxometalate includes a control element of the household appliance. Control elements are elements to be controlled in particular by pressure, proximity or touch, with which operation of the household appliance is generally controlled. Control elements are in particular buttons, switches, toggle handles, rotary selector switches, sliding and rotary controllers, touch-sensitive displays such as in particular touch screens, for instance capacitive touch screens.

Furthermore control units in particular also include door handles, e.g. of a water-bearing household appliance, or a refrigerator or an oven or other handles, which are required in order to use a household appliance, e.g. the handle or a vacuum cleaner or mixing device.

In a further preferred embodiment of the household appliance, an inner surface containing a polyoxymetalate is an inner wall of a water container and/or a throughflow element of the household appliance.

The water container may be for instance the water container of a coffee machine or an automatic coffee maker.

Throughflow elements are generally understood to mean components which are attached to the flow of a watery liquid or a gas in the household appliance. These are preferably grid- or filter-type structures. In such cases, throughflow elements which are already present in the household appliance for other purposes can in accordance with the invention be provided with an inner surface containing a polyoxometalate, or additional throughflow elements containing polyoxometalate on an inner surface can be arranged in the household appliance. By simple modification, an inner surface containing polyoxometalate can be enlarged further in the case of throughflow elements and turbulences in the flowing liquid or gaseous medium can advantageously be generated for an oxidizing reaction on polyoxymetalates.

A throughflow element of the household appliance is in particular an element through which a gaseous or liquid medium flows, and in which microorganisms adhering potentially to an inner wall or other components of a biofilm can be carried along during the flow process. On the other hand, microorganisms or components promoting the growth of microorganisms can be present in gaseous or liquid medium. Throughflow elements within the meaning of the invention are thus in particular fluid lines in a coffee machine, the air-bearing ducts in an extractor hood or the air-bearing ducts in a vacuum cleaner.

In a preferred embodiment, an inventive household appliance includes a container, in which a food is preserved, processed or prepared. "Preserving" here means in particular preserving in a safe environment, for instance in cool or cold environmental conditions which prevent or slow down the spoiling of food. "Processing" means in particular cutting, chopping or mashing food such as vegetables and fruit. "Preparing" for instance means cooking, extracting, boiling and frying a food.

In a preferred embodiment, the household appliance is selected from the group comprising a refrigerator, a coffee machine, an oven, a microwave, a vegetable cutter and a juicer.

In coffee machines and automatic coffee makers, the invention is particularly meaningful to water storage reserves, water lines, strainer carriers, drip shelves, milk frothers and coffee grounds containers. Moreover, the invention is meaningful to kettles, tea infusers and hot water dispensers.

In refrigerators, which also include freezers here, the invention can be used to hygienize the inner surfaces and the condensed water present on the inner surfaces and in the condensed water container and supply lines.

In another preferred aspect, the household appliance claimed herein is a water-bearing household appliance with a container for receiving objects to be treated, which is selected from the group comprising a washing machine, a tumble dryer, a dryer and a dishwasher. Within the meaning of the present invention, such a water-bearing household appliance has at least one outer surface, which contains a polyoxymetalate, e.g. on a control unit or a housing part.

The inventive household appliance may also be a vacuum cleaner and floor care appliance, where surfaces containing the polyoxometalate are in particular in the region of the filter and fleece and of the dust bag and the dust bag receptacle.

Moreover, the inventive household appliance can also be an oven, a microwave or a steamer, a cooker or a hob, wherein the surfaces can be hygienized on account of a polyoxometalate content.

Further examples of inventive household appliances are flow heaters, steam stations and steam irons, air humidifiers, A/C systems and air conditioners. Here both the hygienization of the surfaces and also the water to be heated is of importance. It is generally also important here for the transmission of possibly illness-causing microorganisms or fungi upon skin contact to be prevented by hygienizing the surfaces.

With extractor hoods as a further example of an inventive household appliance, the hygienization of the surfaces, in particular of the filter and the filter mats, and also the disinfecting treatment of air, is of importance.

The polyoxymetalate used within the meaning of the invention can be used in a variety of ways, particularly in the form of particles, as a coating or as part of a coating.

The surface containing polyoxometalate can be generated in any way, provided the inventive catalytic effect is possible. It can be generated for instance by forming a film containing polyoxometalate, or however e.g. by positioning polyoxometalate particles on the surface of a porous material. The generation will depend in particular on the location and type of application.

In a preferred embodiment of the invention, which is particularly suited to use in household appliances, in which liquid or gaseous media, which contain microorganisms or substances promoting their growth, are to be cleaned, the at least one inner surface is formed in the household appliance by particles which contain salt containing at least one polyoxymetalate or consist of the same, wherein the particles are positioned in a filter unit, which is permeable for a gaseous or liquid medium. The filter unit is not restricted here in accordance with the invention, provided the purpose of filtration can be achieved. This can thus be a porous rigid container but also a permeable pocket or envelope made of a fabric.

Particularly if the mode of operation of polyoxometalate is enhanced by contact with an oxidizing agent containing a treatment agent, for instance in the form of a watery solution of the oxidizing agent, the invention enables organic substances such as microorganisms and nutrients to be broken down and thus the formation of a biofilm in the household appliance to be counteracted. In such cases the property of polyoxometalate is used to act in particular as an oxidizing catalyzer. Oxygen radicals (or radicals containing oxygen, subsequently referred to as oxygen radicals") generally form on the inner or outer surface of the household appliance containing polyoxometalate, in the presence of an oxidizing agent like for instance oxygen, hydrogen peroxide or ozone. On account of their chemical reactivity, these oxygen radicals can in particular destroy organic compounds and are consequently damaging to microorganisms. Organic substances for instance in water, which is brought into contact with an inner and/or outer surface of the household appliance coated with polyoxometalate, are in this way broken down and a biofilm thus counteracted.

During the oxidizing reaction, the polyoxometalate is generally used as an oxidizing catalyzer, which acts together with an oxidizing agent. The oxidizing agent is not restricted in accordance with the invention. Oxidizing agents containing oxygen are preferably used. Oxygen, inorganic or organic peroxide and/or ozone are particularly preferable here as oxidizing agents. Oxygen is in turn particularly preferable as an oxidizing agent, since an additional input of possibly damaging or interfering substances can herewith be prevented. Air is used in particular as a source of oxygen.

Ozone is preferred as an oxidizing agent in household appliances with an ozone generator. Household appliances of this type preferably have an ozone elimination apparatus for eliminating excess ozone.

In order to enable a continual oxidizing reaction, sufficient mobility of the oxidizing species, e.g. oxygen radicals, which were generated on the inner surface containing polyoxometalate acting as an oxidizing catalyzer, is to be provided. The degree of the desired mobility generally depends on the application, whether therefore a control element is to be equipped hygienically or whether microorganisms are also to be fought in a surrounding medium.

The inventive household appliance therefore preferably comprises a circulation element and/or air introducing element assigned to the filter unit. The possibility of interacting with a catalytically effective surface containing polyoxometalate is thus increased. Moreover, the possibility of supplying an oxidizing means to the surface containing polyoxometalate is improved. In this way, adequate mobility of the oxidizing species generated on the catalyzer surface, e.g. oxygen radicals, is ensured in order to enable a continuous reaction. Moreover, a sufficiently high oxygen concentration is enabled here, in order to provide as complete a catalyzer reaction as possible.

In a further preferred embodiment of the household appliance, this therefore includes a means of generating or introducing an oxidizing agent, the oxidizing effect of which on microorganisms is enhanced by interaction with the inner or outer surface of the household appliance containing a polyoxymetalate. The oxidizing agent is preferably oxygen, ozone or peroxide here. It is inventively preferred that the inner or outer surface of the household appliance containing the polyoxometalate has a thickness of no more than 50 µm and particularly preferably a thickness of no more than 10 µm.

The subject of the invention is moreover a method for operating a household appliance, which contains at least one catalytically effective substance in a surface, wherein the catalytically effective substance is a polyoxometalate, which is contained in an inner and/or outer surface of the household appliance, provided that the polyoxometalate is contained at least in an outer surface of the household appliance, if the household appliance is a water-bearing household appliance with a container for receiving objects to be cleaned, and wherein an inner and/or outer surface containing polyoxometalate is treated with a treatment agent which contains an oxidizing agent.

Oxygen radicals form for instance on an inner or outer surface of the household appliance containing a polyoxometalate in the presence of an oxidizing agent, which is dissolved in water for instance or can be mixed in water or air. If these very reactive oxygen radicals come into contact with organic substances, including microorganisms, an oxidizing reaction ensues, which results in the breakdown of organic substances and/or in pathological processes in the microorganisms. The formation of a biofilm is in this way counteracted.

In a preferred embodiment, as already mentioned, an oxidizing agent containing oxygen is used, in particular oxygen wherein air is used as a source of oxygen. In such cases the oxygen may be present dissolved in the water for instance. Moreover, by correspondingly moving air containing oxygen or water containing oxygen, a mixture of air and water may result, for instance forming air bubbles in the water. Such an air-water mixture can be brought into contact with the surface containing polyoxometalate, wherein the air oxygen is used as an oxidizing agent.

In a further preferred embodiment of the method, a peroxide or ozone is used as an oxidizing agent. Ozone can advantageously be used as an oxidizing agent in devices with ozone generators. The surface containing polyoxometalate is then arranged such that it can come into contact with ozone.

The invention is advantageous in that a household appliance is made available in a simple and cost-effective manner, which has less of a tendency towards contamination, in particular also with microorganisms, and is easier to clean in the event consequently of contamination developing.

In such cases a particular advantage of the use of inner and outer surfaces containing polyoxometalate consists in these being able to function as a catalytic system for years, without an additional activation or an additional energy consumption being required. Additional energy consumption would only take place when an additional circulation or air introduction element is used, wherein this is minimal compared with other cleaning methods. Moreover, no additional reactants need to be added and an activation of the catalyzer, for instance by means of UV radiation, is omitted. Moreover, polyoxometalates may have a virucidal effect. Therefore the present invention provides a hygiene system for household appliances almost without running costs and with a long service life.

The cleaning process is less complicated on account of the special surfaces. In particular, cleaning may be required less frequently or not at all. Moreover, the invention also enables a remote action in the sense that only surfaces containing polyoxometalate are protected or are easily freed of microorganisms. The oxidizing reactions taking place on surfaces containing polyoxometalates can also influence adjacent regions in a household appliance and combat microorganisms there.

The invention claimed is:

1. A household appliance having an inner surface and an outer surface, the household appliance containing at least one catalytically effective substance in a surface, wherein the catalytically effective substance is a polyoxometalate, wherein the polyoxometalate is contained at least in the outer surface of the household appliance, wherein the outer surface of the household appliance is a surface which is accessible to a user of the household appliance during conventional operation of the household appliance without interfering with operation, and wherein the inner surface of the household appliance is a surface which is not accessible to a user of the household appliance during conventional operation of the household appliance without interfering with the operation.

2. The household appliance as claimed in claim 1, wherein the polyoxometalate is wolframate.

3. The household appliance as claimed in claim 2, wherein the polyoxometalate contains vanadium.

4. The household appliance as claimed in claim 3, wherein the wolframate includes the $[SiV_3W_9O_{40}]^{7-}$ anion.

5. The household appliance as claimed in claim 2, wherein the wolframate is titanium-modified.

6. The household appliance as claimed in claim 1, wherein the outer surface containing polyoxymetalate includes a control element of the household appliance.

7. The household appliance as claimed in claim 1, wherein the inner surface contains polyoxometalate and is an inner wall of a water container and/or a throughflow element of the household appliance.

8. The household appliance as claimed in claim 1, wherein the household appliance includes a container, in which a food is stored, processed or prepared.

9. The household appliance as claimed in claim 8, wherein the household appliance is selected from the group comprising a refrigerator, a coffee machine, an oven, a microwave, a vegetable cutter and a juicer.

10. The household appliance as claimed in claim 1, wherein the household appliance is a water-bearing household appliance with a container for receiving objects to be treated, which is selected from the group comprising a washing machine, a tumble dryer, a dryer and a dishwasher.

11. The household appliance as claimed in claim 1, wherein the inner surface is formed by particles, which contain at least one salt containing polyoxometalate or consist of the same, wherein the particles are positioned in a filter unit, which is permeable for a gaseous or liquid medium.

12. The household appliance as claimed in claim 11, wherein the household appliance has a circulation element and/or air introduction element assigned to the filter unit.

13. The household appliance as claimed in claim 1, further comprising an oxidizing agent, the oxidizing effect of which on microorganisms is enhanced by interaction with the inner or outer surface of the household appliance containing a polyoxymetalate.

14. The household appliance as claimed in claim 13, wherein the oxidizing agent is oxygen, ozone or a peroxide.

15. The household appliance as claimed in claim 1, wherein the polyoxometalate is present at least partially as tetra-alkylammonium salt.

* * * * *